(12) United States Patent
Bonnefous

(10) Patent No.: US 6,508,769 B2
(45) Date of Patent: Jan. 21, 2003

(54) ULTRASONIC IMAGE PROCESSING METHOD AND EXAMINATION SYSTEM FOR DISPLAYING AN ULTRASONIC COLOR-CODED IMAGE SEQUENCE OF AN OBJECT HAVING MOVING PARTS

(75) Inventor: Odile Bonnefous, Nogent-sur-Marne (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 105 days.

(21) Appl. No.: 09/746,552

(22) Filed: Dec. 28, 2000

(65) Prior Publication Data

US 2001/0031921 A1 Oct. 18, 2001

(30) Foreign Application Priority Data

Dec. 28, 1999 (EP) .............................. 99403309

(51) Int. Cl.[7] ................................. A61B 8/00
(52) U.S. Cl. ..................... 600/447; 600/450; 600/454
(58) Field of Search ................... 600/441, 553, 600/437, 450, 440

(56) References Cited

U.S. PATENT DOCUMENTS 5,355,887 A * 10/1994 Iizuka et al. ............... 600/440
5,579,771 A    12/1996 Bonnefous ............. 128/661.04

* cited by examiner

Primary Examiner—Marvin M. Lateef
Assistant Examiner—Ruby Jain
(74) Attorney, Agent, or Firm—John Vodopia

(57) ABSTRACT

An ultrasonic image processing method includes acquiring ultrasonic signals related to an object having moving parts in a medium; constructing an ultrasonic grayscale 2-D image sequence representing a cross-section of a segment of the object with respect to a longitudinal axis (X) perpendicular to the grayscale image lines (Z); estimating the displacements and the displacement gradients of a boundary of the object; and normalizing the gray levels in a boundary zone and color-coding the points of the boundary zone of an image sequence as a function of the displacement gradient values, in order to provide color-coded information of the object moving parts displacement variations. An ultrasonic examination imaging system for carrying out the method having a color display system is also disclosed.

15 Claims, 4 Drawing Sheets

ULTRASONIC IMAGE PROCESSING METHOD AND EXAMINATION SYSTEM FOR DISPLAYING AN ULTRASONIC COLOR-CODED IMAGE SEQUENCE OF AN OBJECT HAVING MOVING PARTS

DESCRIPTION

The invention relates to an ultrasonic image processing method for displaying an ultrasonic examination color-coded image sequence of an object having moving parts in a medium. The invention also relates to an ultrasonic examination imaging system for carrying out this method.

The invention is used in the field of ultrasonic diagnostic imaging, for providing cardiovascular non-invasive diagnostic tools for studying anomalies of arteries and notably stenoses. A basic diagnostic criterion for a stenosis is an abrupt reduction of the diameter of a suspect artery segment observed in an artery image. A more elaborate criterion is the study of the artery wall displacements in function of the instants of the cardiac cycle and in function of the location along the artery segment. Therefore, in order to early diagnosing stenosed arteries, the medical field has a need for non-invasive means for providing artery images together with readily visible indications related to the arterial wall displacements.

An ultrasonic image processing method for calculating wall displacements of an artery segment is already known from the patent U.S. Pat. No. 5,579,771 (Bonnefous, Dec. 3, 1996). This document describes a method for characterizing an artery segment by ultrasonic imaging, using an array of ultrasonic transducers that produces a sectional frame, which is formed by image lines of a number of successive parallel excitation lines extending perpendicularly to the artery axis. Said array is coupled to a transmitter/receiver circuit, which provides high frequency signals to a signal processing system. Said system determines the arterial wall velocities and displacements, in the arterial radial direction Z, at a given location corresponding to an excitation line along the longitudinal X-axis of the artery, in function of excitation instants t, during a cardiac cycle. So, FIG. 1 of this document shows a system in a block diagram form, apt to carry out this method.

So, under the influence of the pulsating wave of the blood in the artery during a cardiac cycle, the walls of the artery are subject to periodic radial movements whose amplitude and velocity can be determined. Depending on the state of the arterial walls, the pressure variations induced by the pulsating wave create either a uniform arterial dilatation or distorted parietal movements. Evaluating the distortions or non-distortions of the artery walls permits of deriving the presence and seriousness of stenosis, or elasticity defects, in real time, enabling optimization of the diagnosis. To that end, it is important to obtain information about the arterial wall movements and it is still more important to obtain information about the wall movement variations, i.e the movement gradients.

So, a problem lies in the fact that the movement gradients are not readily exploitable by a cardiologist. Not only the arterial wall movement variations must be made easily available and exploitable, but also, concomitantly, a standard grayscale image of the corresponding artery segment must be displayed, in order to perform a successful study and a precise diagnosis of the suspect zone of artery.

Now, a further problem lies in the fact that the gradient information, which is to be further added to the grayscale image, must not make this grayscale image unreadable.

SUMMARY OF THE INVENTION.

The problems discussed above are solved by means of a method as disclosed herein.

An advantage of the method of the present embodiments is that the arterial wall behavior is made clearly visible together with the gradient information that is strongly related to arterial wall lesions. This is most useful to establish a diagnosis. Another advantage is that non-invasive means are used, which permit avoiding a modification of the artery pressure, hence the actual wall movements, as would be the case using invasive means.

An ultrasonic diagnostic system having means for carrying out the method is also disclosed.

BRIEF DESCRIPTION OF THE FIGURES

Specific embodiments of the invention will be described in detail hereinafter with reference to the accompanying diagrammatic drawings wherein.

DESCRIPTION OF THE PREFERRED EMBODIMENTS

Figure 1A:
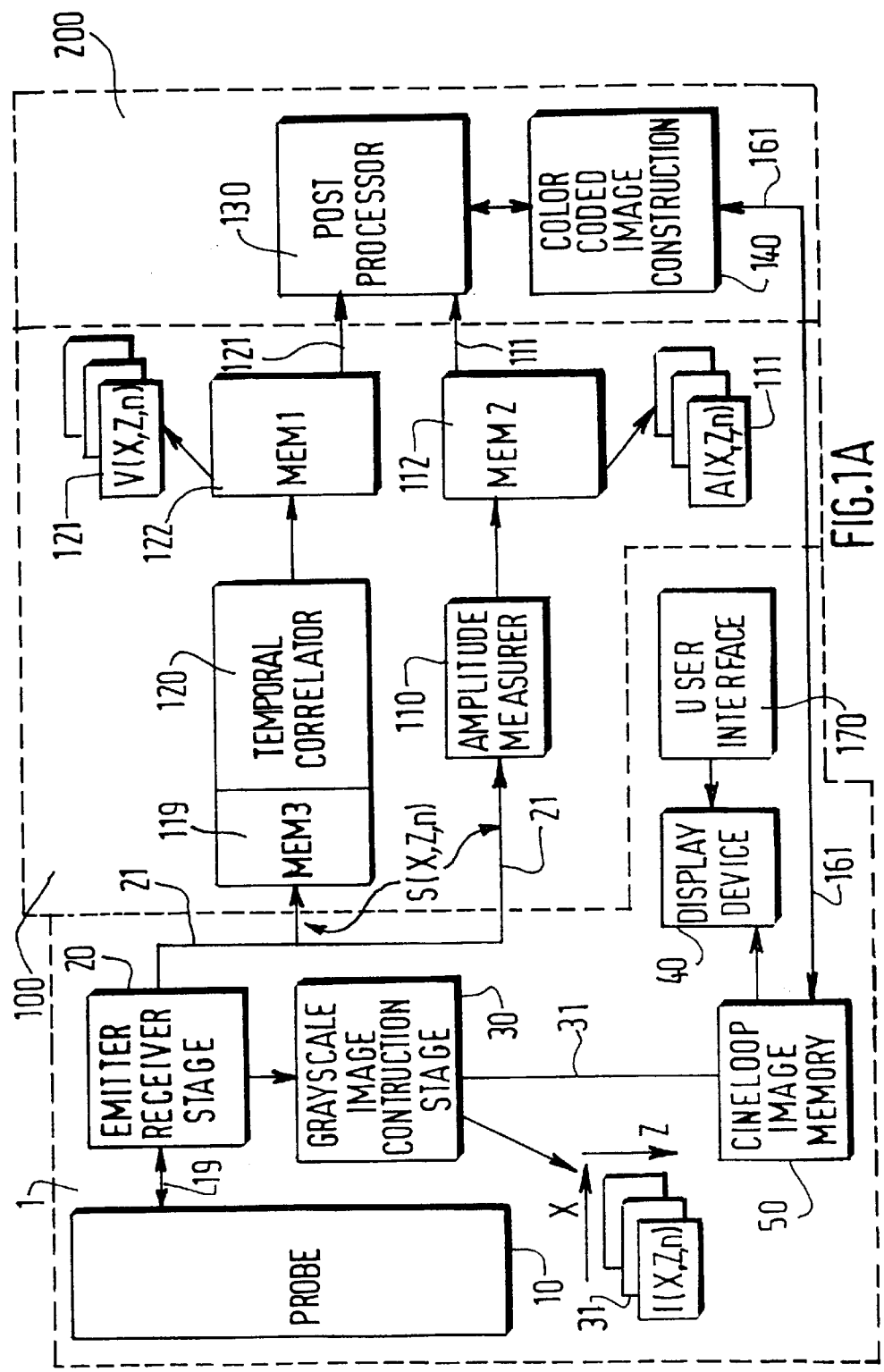
FIGS. 1A, 1B, 1C show block diagrams of an ultrasonic diagnostic imaging system for carrying out a color-coded image sequence construction method.
Figure 1B:
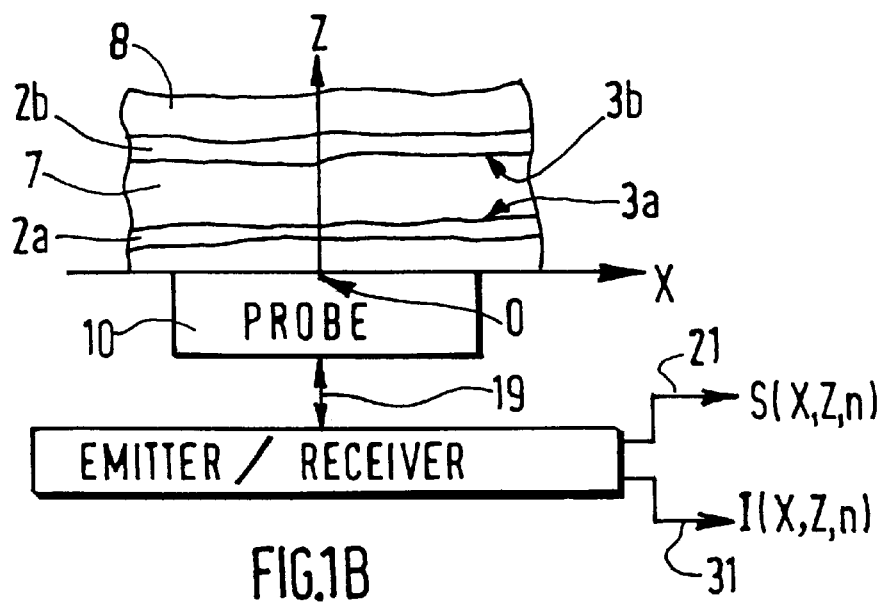
Figure 3:
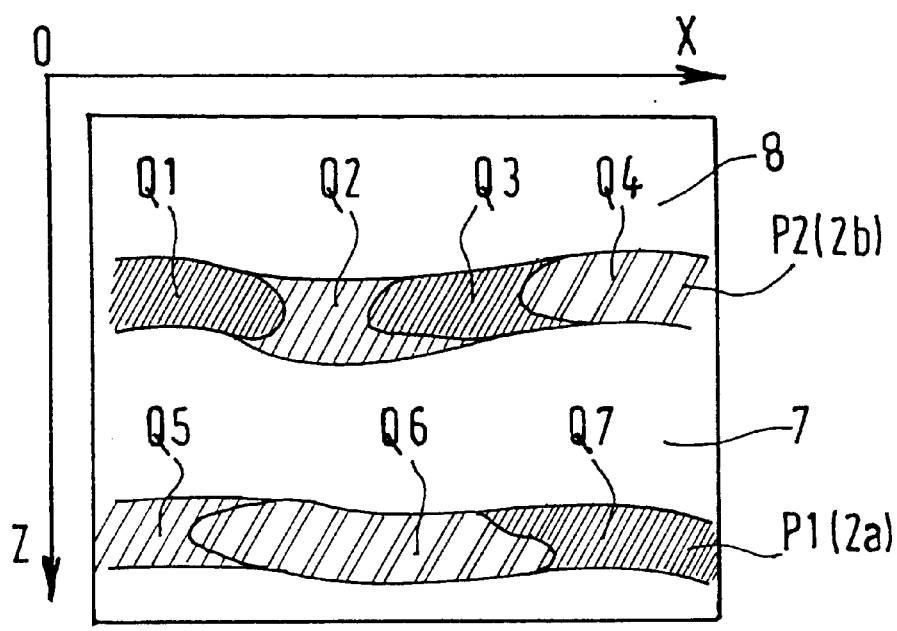
FIG. 3 shows an image constructed using the method.

Referring to FIG. 1A and 1B, an ultrasonic diagnostic imaging system, shown in a block diagram form, is used as a tool for the examination of an artery 7 located in a medium 8 and comprises sub-systems 1, 100, 200 to perform an image processing method for the construction and display of a sequence of images, which permits of visualizing together:

an arterial segment whose walls have radial displacements occurring under the influence of the blood pressure, in function of the different time instants of a cardiac cycle, and color-coded information related to the displacement variations along the longitudinal axis of the artery, as illustrated by FIG. 3.

Referring to FIG. 1A and FIG. 1B, this image processing method comprises a step 1 of acquiring ultrasonic signals related to the artery segment, said artery segment having a longitudinal axis denoted X-axis and a radial axis denoted Z-axis, a step 100 of determining the arterial wall displacement gradients and a step 200 of constructing and displaying a sequence of color-coded images comprising a display of a grayscale image sequence representing said artery segment, in which specific zones of the arterial walls, are color-coded in function of the values of the wall displacement gradients. In the sequence of color-coded images, which is registered during a whole cardiac cycle, each image is acquired at a given instant n of said cardiac cycle.

The grayscale sequence images show that each arterial wall has radial displacements denoted D(Z,X,n), from one image to the other; it means that a point situated on the internal boundary of the wall, at a given location X, is submitted to a displacement along the Z-axis. The color-coded representation of the specific zones of the walls, preferably in red, gives the information constituted by the local wall displacement variations, meaning the variation Δ of the estimated radial displacements D(Z,X,n) around said location X.

Referring to FIG. 1A and 1B, the method of forming the sequence of ultrasonic color-coded images by forming an ultrasonic grayscale image sequence of the moving artery, where the zones of high movement gradients related to local high strains in the arterial walls are displayed in color, for example red, comprises the particular steps of:

acquisition 30 of the ultrasonic gray image sequence;

segmentation 62 of the gray image sequence to identify the arterial walls by determining transition lines 3a, 3b between the interior of the artery and the artery walls;

computation 68, 69 of the arterial wall displacements D(Z,X,n) at each instant n;

computation 71,73 of the wall displacement gradients Δ=d(D)/dX at each instant n.

Figure 2A:
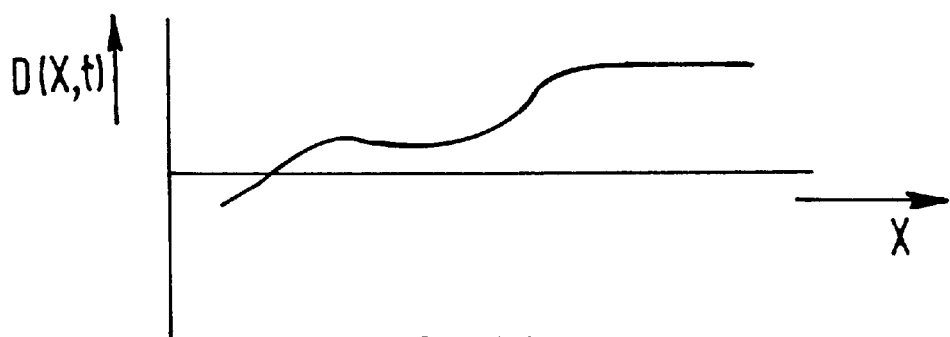
FIGS. 2A and 2B show respectively artery wall displacement and displacement gradient curves.
Figure 2B:
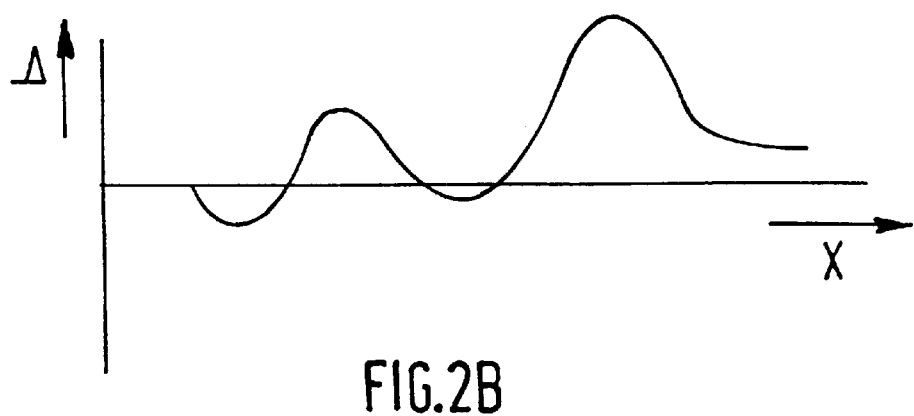
Figure 2C:
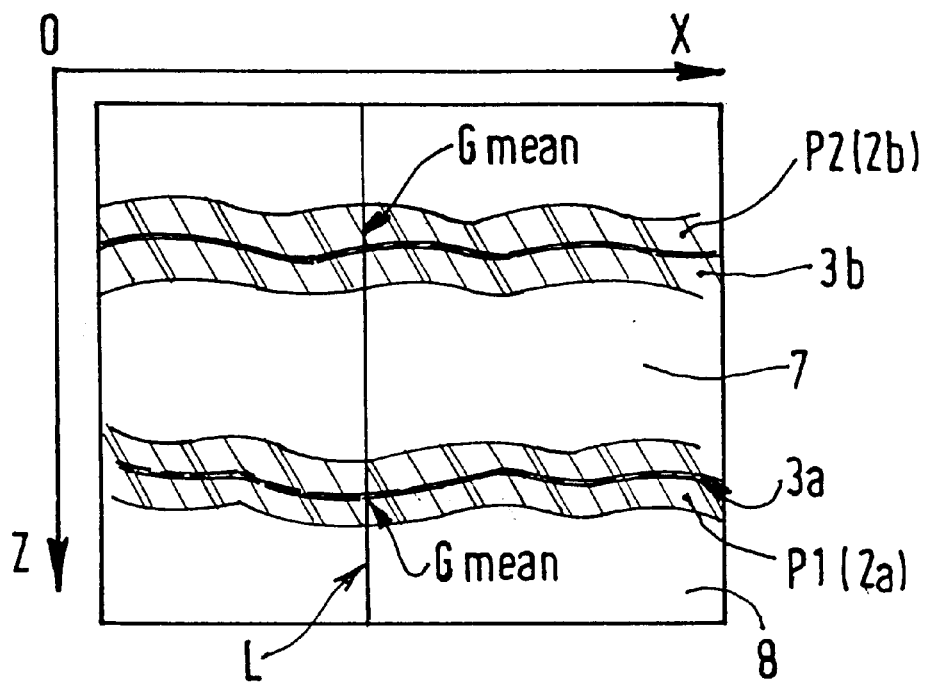
FIG. 2C illustrates the construction of a color-coded image.

Illustrated by FIG. 2C, this method further comprises a step 140 performing the normalization of the gray images on the location of arterial wall in order to solve a problem lying in that the ultrasonic grayscale image must remain visible when the specific zones are colored; this step comprises sub-steps of making whiter the boundary zones of the artery walls and assuring sufficient transparency of the colored zones, wherein:

evaluation of ribbon-shaped zones P1, P2 spanning both sides of each transition line 3a, 3b, for instance 1 mm each side, that is 2 mm wide and computation of the mean gray values denoted $G_{mean}$ for each pixel in the ribbon-shaped zones, which is performed by evaluating the mean gray value on each excitation line L parallel to the Z-axis in said zones;

estimation of new gray values G for each pixel in the ribbon-shaped zones P1, P2, based on the original gray values denoted $G_0$, taking into account the mean gray values $G_{mean}$, in order to reinforce the white in said zones, for example using the following formula in an image supposed to have 256 gray levels: G.=128 ($G_0$/$G_{mean}$). As G is made larger, the image in made whiter in the ribbon-shaped zones.

Illustrated by FIG. 3, the step 140 of the method further performs coloring the points in said ribbon-shaped zones P1, P2 in function of the displacement gradients. Before coloring the zones, the gray value of each point results of the association of three color components as follows: G=V=B=R where G is for gray, V for green, B for blue and R for red. For coloring of the gradient zones, the level of each color component is modified as follows: R=G, V=G (1−Δ/256), B=G (1−Δ/256), if the number of gray-levels is 256, so as a point in the boundary zone has a color C given by associating the new levels of the components R, V, B. Other color-coding methods are possible to those skilled in the art. However, the proposed method gives good results for studying the displacement variations based on the display of the artery grayscale images with color-coded wall displacement gradients. FIG. 3 illustrates a resulting image by representing the different color-coded zones by different striped zones Q1 to Q7, corresponding to different displacement gradients.

FIG. 1A shows the ultrasonic diagnostic imaging system for the formation and display of the sequences of composite images as above-described, comprising the display of grayscale images with color-coded information of the movement gradients of the artery walls over at least one cardiac cycle. So, this ultrasonic diagnostic imaging system constitutes a tool for the diagnosis of lesions of arterial walls. This ultrasonic diagnostic imaging system comprises sub-systems 1, 100, 200.

Referring to FIG. 1A, the operation of the sub-system 1 involves an ultrasonic probe 10 in contact with the medium 8 observed. The ultrasonic probe 10 transmits, via periodic excitations, ultrasonic signals to the medium scanned, in a direction OZ, and receives, in the same direction OZ, the echoes returned by the obstacles encountered in the medium. The probe is preferably composed of ultrasonic transducers which are assembled in a linear array parallel to the X-axis. A respective excitation line corresponds to each transducer.

Referring to FIG. 1B, the examination of the medium by the ultrasonic probe 10 is performed in such a manner that the artery 7 is scanned longitudinally in the direction parallel to OX in order to obtain longitudinal cross-sectional intensity images, enabling the visualization of the front wall 2a and the rear wall 2b. The direction of the transducer array is represented by the direction OX and the direction of the excitation lines is represented by the direction OZ. Therefore, the echographic image is scanned along the excitation lines of direction OZ which are the columns of the image. The probe is connected in 19 to an emitter/receiver stage 20. In a transmission step, the medium is scanned along the directions of the excitation lines. In a receiving step, the image of each excitation line is formed, taking into account the propagation time in the medium and the amplitude of the echoes returned by the obstacles encountered along the excitation line considered. Preferably, in order to obtain a suitable resolution for the image, the ultrasonic excitations are focused during transmission as well as reception. The emitter/receiver stage 20 provides acoustic high-frequency signals S(X,Z,n) which enable the formation, as a function of the instant n, of a sequence of intensity images I(X,Z,n) by way of an operation 30, n being the number of the image of the sequence. Each intensity image I(X,Z,n) 21 is thus formed by the scanning of the excitation lines of the probe. The behavior of the artery is observed at least over a full cardiac cycle. Therefore, a sequence of a number N of images covering a time interval which is at least equal to a cardiac cycle is formed, N being a number 1≦N. The number of image excitation lines may be, for example 68 or 112 with a scanning step (distance between excitation lines) of 0.5 mm or 0.25 mm. These characteristics enable visualization of an arterial segment of 28 mm.

Referring to FIG. 1A, the intensity images I(X,Z,n) 21 referred to as grayscale images are stored in an image memory 50 denoted Cineloop for further construction of the display of color-coded images. For the evaluation of the displacement gradients, it is necessary to determine the velocity and the amplitude of the displacements of the walls.

The sub-system 100 includes a processor which executes the steps of processing the high-frequency signals S(X,Z,n). The sub-system 100 first performs a temporal correlation operation 120. The successive ultrasonic echoes are compared by way of their correlation function. The displacement of the biological structures from one ultrasonic emission to the next is estimated while taking into account the displacement of the correlation peak corresponding to the delay introduced by this displacement upon reception. For all objects scanned, the correlation operation 120 provides velocity measurements in the form of two-dimensional velocity images V(X,Z,n) denoted 121. The correlation function is performed between the images of the image sequence. So, a rather large memory 119 denoted MEM3 must be available at the input of the module 120 performing the correlation operation for providing the necessary delay between two correlated signals.

Besides the velocity images 121 V(X,Z,n), echo amplitude images 111 A(X,Z,n), used as segmentation means, are also necessary to perform the further extraction and localization of the parietal velocities of the two-dimensional velocity images. These amplitude images 111 A(X,Z,n) are obtained, in the sub-system 100, by means of an amplitude measurer 110. The memory 122 called MEM1 and the memory 112 called MEM2 store the results of the sub-system 100, which are respectively the velocity images V(X,Z,n) and the echo amplitude images A(X,Z,n).

Figure 1C:
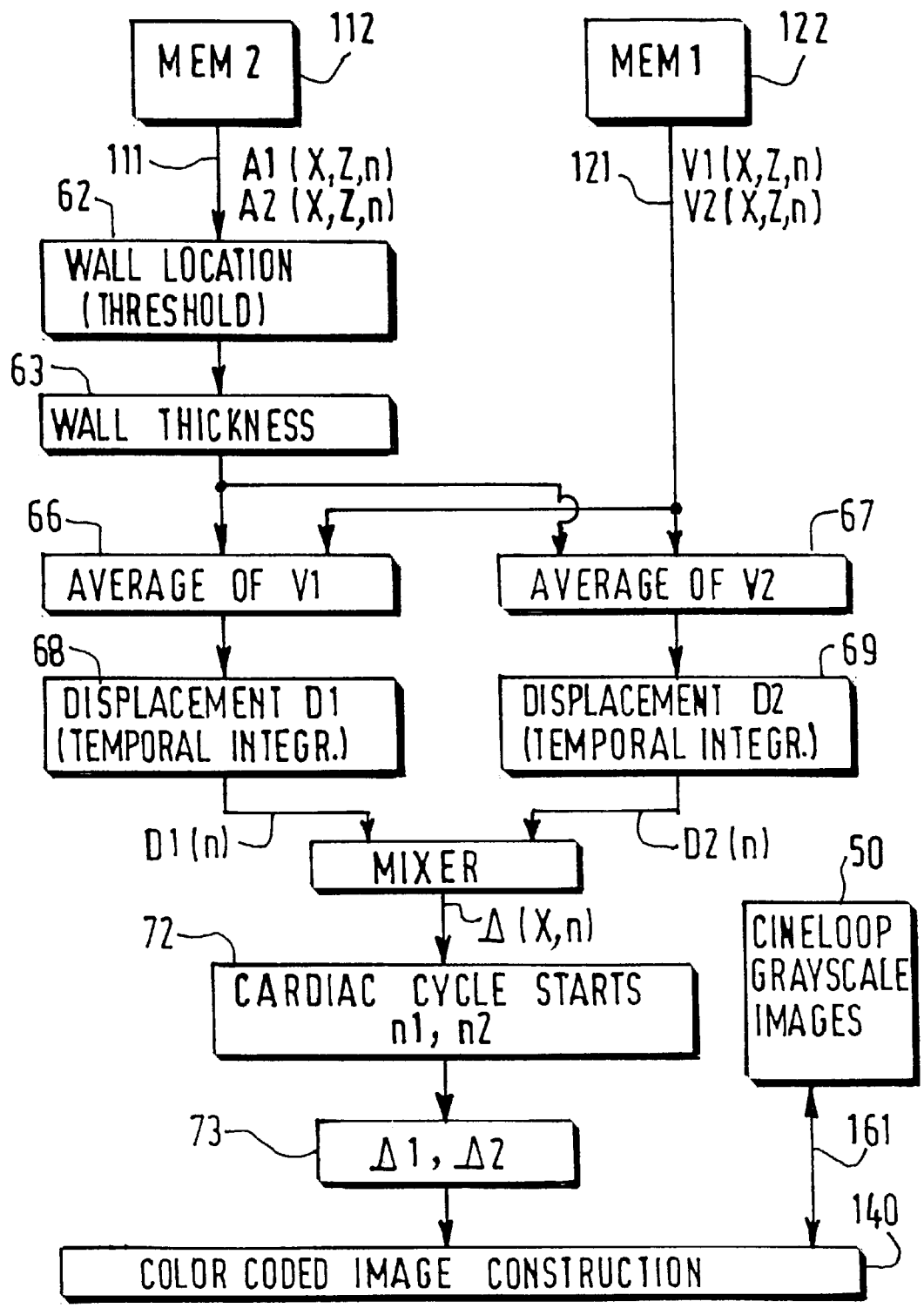

Referring to FIG. 1C, the sub-system 200 comprises a processor, which executes the post-processing operation 130 applied to the results of the preceding operations 110 and 120 in order to determine the upper and lower wall displacements respectively D1(X,n) and D2(X,n), and the corresponding displacement gradients Δ1(X,n), Δ2(X,n). The operation 130 comprises steps of:

application 62 of an adaptable threshold for each amplitude image 111 A(X,Z,n) in order to perform the identification of the internal parietal boundary of the artery: this threshold produces digital images with black/white transitions between the interior and the exterior of the artery corresponding to the lower and upper internal parietal boundaries 3a, 3b; these transitions are filtered to eliminate discontinuities;

determination 63 of the respective thickness of each arterial walls. In the current implementation, a thickness value amounts to approximately 1 mm; determination 66, 67 of an average value of the velocities through the thickness of the arterial wall, for example through the given thickness of 1 mm;

determination 68, 69 of the displacements D1(X,n) and D2(X,n) between each image, related to each wall, by a temporal integration, such as shown by the curve of FIG. 2A; and determination of the corresponding displacement gradients Δ1(X,n), Δ2(X,n) for each wall, calculated by an adder 71 as the difference between two displacement values, such as shown by the curve of FIG. 2B.

After corrections in 73, taking into account the starting instants n1, n2 of the cardiac cycles determined in 72, where the artery has zero parietal displacements, the display sequence images, as shown in FIG.3, are constructed by the module 140, which constructs the color-coded zones corresponding to the parietal displacement gradients Δ1(X,n), Δ2(X,n) at the instant n in the grayscale images I(X,Z,n) fetched from the memory 50 Cineloop.

Referring to FIG. 1A, the ultrasonic processing system also comprises an interface 170 for the user to control the display of the images of the sequence in function of the time instants n. The display system, the processors and the memories may respectively be the screen 40, the processor 130 and the memory of a workstation as known of those skilled in the art. The workstation may also comprise a keyboard and a mouse used as an interface for the user to control the image of the screen. A color display system is used to display the color-coded zones.

The invention can be applied to the processing of signals different from ultrasonic signals, for example electric, electromagnetic signals, etc, and to the processing of other objects other than an artery, for example objects having moving parts with regularly recurring displacements. During the display of the sequence on the display device 40, the physician can qualitatively and quantitatively evaluate the distortions or non-distortions of the displacements of the walls and derive therefrom the presence and the seriousness of stenosis, or elasticity defects, linked to the arterial walls of the subjacent grayscale image, in real time, which enables optimization of the diagnosis.

What is claimed is:

1. Ultrasonic image processing method comprising:
acquiring ultrasonic signals related to an object having moving parts in a medium; constructing an ultrasonic grayscale 2-D image sequence representing a cross-section of a segment of the object with respect to a longitudinal axis (X) perpendicular to grayscale image lines (Z); estimating displacements and displacement gradients of a boundary of the object; and normalizing gray levels in a boundary zone and color-coding points of the boundary zone of the image sequence as a function of the displacement gradients, in order to provide color-coded information of displacement variations of the object moving parts.

2. A method as claimed in claim 1, wherein the object is an artery, the moving parts are the artery walls moving under the blood pressure, the displacements are periodic due to cardiac cycles, the grayscale image longitudinal axis (X) is an artery axis, the displacements are radial arterial displacements and gradients of wall displacement are color-coded to provide information on the arterial wall displacement variations.

3. An ultrasonic examination imaging system to carry out a method according to claim 1, comprising an ultrasonic probe coupled to an ultrasonic system for emitting and receiving ultrasonic signals from a medium of an object having moving parts, and comprising ultrasonic sub-systems to process the received ultrasonic signals with processors to construct color-coded images, memories to store the images, a display system to display the color-coded images.

4. A system as claimed in claim 3, wherein the display system is a color system.

5. A system as claimed in claim 3, comprising a suitably programmed computer of a workstation or a special purpose processor having circuit means, which are arranged to process ultrasonic signals according to said method, said system having means to display the images constructed according to said method, and having a user interface to permit a user control of the display.

6. A computer program product comprising a set of instructions for carrying out the method as claimed in claim 1.

7. Ultrasonic image processing method comprising:
acquiring ultrasonic signals related to an object having moving parts in a medium; constructing an ultrasonic grayscale 2-D image sequence representing a cross-section of a segment of the object with respect to a longitudinal axis (X) perpendicular to grayscale image lines (Z); estimating displacements and displacement gradients of a boundary of the object; and normalizing gray levels in a boundary zone and color-coding points of the boundary zone of the image sequence as a function of the displacement gradients, in order to provide color-coded information of displacement variations of the object moving parts, wherein the grayscale image normalization step comprises sub-steps of segmentation of the grayscale images to determine a boundary transition line, estimation of the boundary zone as a zone spanning each side of the boundary transition line, estimation of a mean gray ($G_{mean}$) level in the boundary zone and calculation of new gray values (G) for the points of the boundary zone, based on estimated mean gray values and on original gray values ($G_0$), which are on average whiter than the original gray values.

8. A method as claimed in claim 7, wherein the new gray values G for the points of the boundary zone are estimated using the following relation: $G=128 (G_0/G_{mean})$ where $G_0$ is the original gray value and $G_{mean}$ is the mean gray value on the corresponding line of the grayscale image in the boundary zone.

9. A method as claimed in claim 7, wherein the color-coding step comprises sub-steps of estimating a new color of the points in the boundary zone by varying the levels of the color components (R, B, V) of the new gray color levels (G) at said points as a function of the displacement gradients ($\Delta$).

10. A method as claimed in claim 9, wherein, each gray point is formed by association of three color components as follows: G=V=B=R where G is for gray, V for green, B for blue and R for red, the levels of each color component are modified and the new levels are given by the following relations: R=G, V=G (1−$\Delta$/256), B=G (1−$\Delta$/256), wherein the number of gray-levels is 256, so that a point in the boundary zone has a new color C given by associating the new levels of the components R, V, B.

11. A method as claimed in claim 7, wherein the object is an artery, the moving parts are the artery walls moving under the blood pressure, the displacements are periodic due to cardiac cycles, the grayscale image longitudinal axis (X) is an artery axis, the displacements are radial arterial displacements and gradients of wall displacement are color-coded to provide information on the arterial wall displacement variations.

12. An ultrasonic examination imaging system to carry out a method according to claim 2, comprising an ultrasonic probe coupled to an ultrasonic system for emitting and receiving ultrasonic signals from a medium of an object having moving parts, and comprising ultrasonic sub-systems to process the received ultrasonic signals with processors to construct color-coded images, memories to store the images, a display system to display the color-coded images.

13. A system as claimed in claim 12, wherein the display system is a color system.

14. A system as claimed in claim 12, comprising a suitably programmed computer of a workstation or a special purpose processor having circuit means, which are arranged to process ultrasonic signals according to said method, said system having means to display the images constructed according to said method, and having a user interface to permit a user control of the display.

15. A computer program product comprising a set of instructions for carrying out the method as claimed in claim 7.

* * * * *